United States Patent
Graziano

(10) Patent No.: US 9,326,504 B1
(45) Date of Patent: May 3, 2016

(54) DISPOSABLE ANTIBACTERIAL LINER

(71) Applicant: Christine Graziano, Pembroke, MA (US)

(72) Inventor: Christine Graziano, Pembroke, MA (US)

(*) Notice: Subject to any disclaimer, the term of this patent is extended or adjusted under 35 U.S.C. 154(b) by 0 days.

(21) Appl. No.: 14/747,355

(22) Filed: Jun. 23, 2015

(51) Int. Cl.
*A01N 25/34* (2006.01)
*A01N 33/12* (2006.01)
*A41D 27/10* (2006.01)

(52) U.S. Cl.
CPC ............... *A01N 25/34* (2013.01); *A01N 33/12* (2013.01); *A41D 27/10* (2013.01)

(58) Field of Classification Search
None
See application file for complete search history.

(56) References Cited

U.S. PATENT DOCUMENTS

| | | | |
|---|---|---|---|
| 3,817,702 A * | 6/1974 | Pauli | D06M 16/00 424/404 |
| 5,071,698 A | 12/1991 | Scheerder | |
| 5,899,207 A | 5/1999 | Scheinberg | |
| 6,067,987 A | 5/2000 | Scheinberg | |
| 6,548,138 B2 * | 4/2003 | Abiko | G11B 7/007 428/64.1 |
| 6,596,681 B1 * | 7/2003 | Mahieu | C11D 1/83 15/209.1 |
| 6,994,681 B2 | 2/2006 | Slautterback | |
| 7,479,577 B2 | 1/2009 | Scheinberg | |
| 7,682,994 B2 * | 3/2010 | Van Emden | A41D 31/02 264/103 |
| 8,100,847 B2 | 1/2012 | Fournet, II | |
| 8,323,226 B1 | 12/2012 | Roche | |
| 8,790,287 B2 | 7/2014 | Evans | |
| 2009/0200328 A1 * | 8/2009 | Hoefing | B65H 75/16 221/33 |

FOREIGN PATENT DOCUMENTS

CA 2529711 C 1/2014

* cited by examiner

*Primary Examiner* — Robert A Wax
*Assistant Examiner* — Melissa Mercier
(74) *Attorney, Agent, or Firm* — Kyle A. Fletcher, Esq.

(57) ABSTRACT

The disposable antibacterial liner is a skin covering that provides a protective barrier between the skin and the personal protective equipment. The disposable antibacterial liner is a sheath that is worn between the skin and the personal protective equipment. The sheath is treated with an antimicrobial finish that both 1) acts as a prophylaxis that protects the skin from infection; and, 2) treats the personal protective equipment 133 with the antimicrobial finish to help keep the personal protective equipment 133 clean. The disposable antibacterial liner comprises a sheath and an antimicrobial finish. Alternate embodiments of the disclosure further comprise a container and perforations within the sheath.

17 Claims, 3 Drawing Sheets

DISPOSABLE ANTIBACTERIAL LINER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

The present invention relates to the field of medical bandages and medical applicators, more specifically, a disposable antibacterial liner configured for use with sporting equipment.

Because of the high expense of personal protective equipment, the regular and repeated use of personal protective equipment during occupational or sporting activities is often required. Given the difficulty of cleaning personal protective equipment and the propensity to store personal protective equipment in dark and enclosed locations the sweat that accumulates on the personal protective equipment often provides an ideal environment for the establishment of bacterial and other microbial colonies. The constant contact of the wearer's skin against the personal protective equipment will often cause the development of contact dermatitis, which increases the risk of further infections.

SUMMARY OF INVENTION

The disposable antibacterial liner is a skin covering that provides a protective barrier between the skin and the personal protective equipment. The disposable antibacterial liner is a sheath that is worn between the skin and the personal protective equipment. The sheath is treated with an antimicrobial finish that both 1) acts as a prophylaxis that protects the skin from infection; and, 2) treats the personal protective equipment with the antimicrobial finish to help keep the personal protective equipment clean.

These together with additional objects, features and advantages of the disposable antibacterial liner will be readily apparent to those of ordinary skill in the art upon reading the following detailed description of the presently preferred, but nonetheless illustrative, embodiments when taken in conjunction with the accompanying drawings.

In this respect, before explaining the current embodiments of the disposable antibacterial liner in detail, it is to be understood that the disposable antibacterial liner is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the disposable antibacterial liner.

It is therefore important that the claims be regarded as including such equivalent construction insofar as they do not depart from the spirit and scope of the disposable antibacterial liner. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
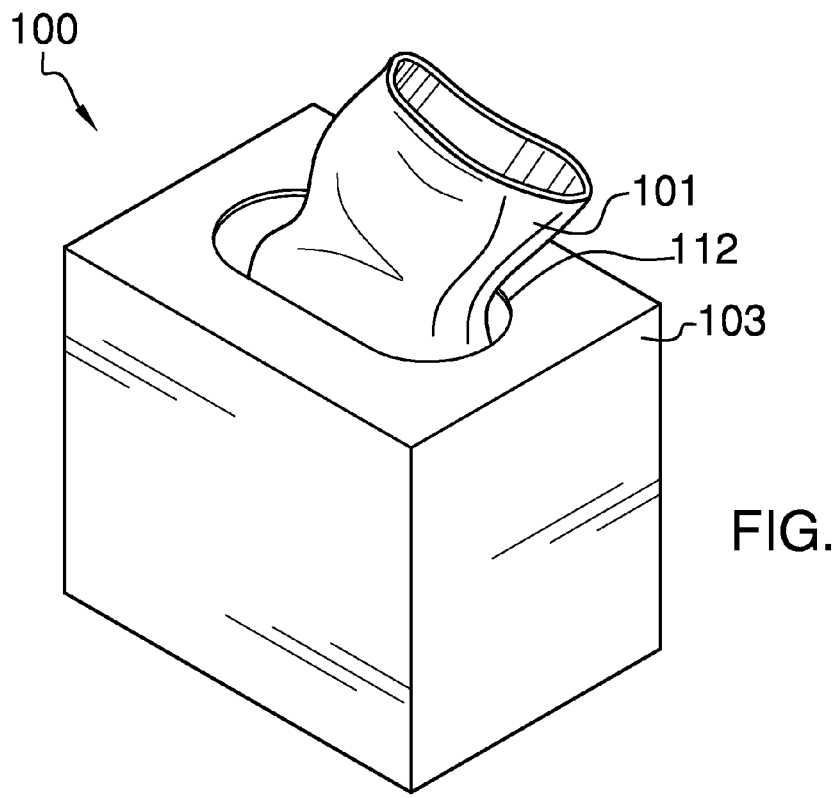
FIG. 1 is a perspective view of an embodiment of the disclosure.
Figure 2:
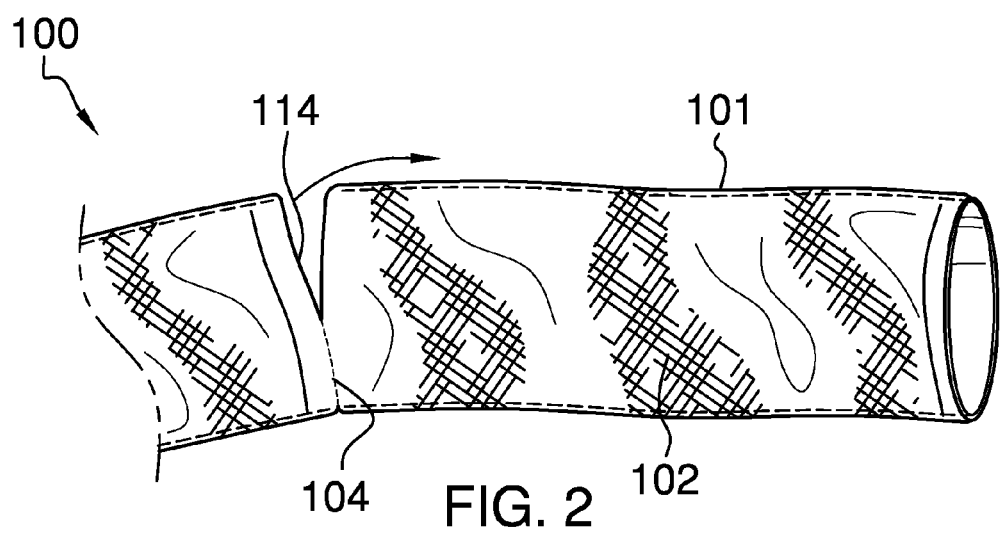
FIG. 2 is a detail view of an embodiment of the disclosure.
Figure 3:
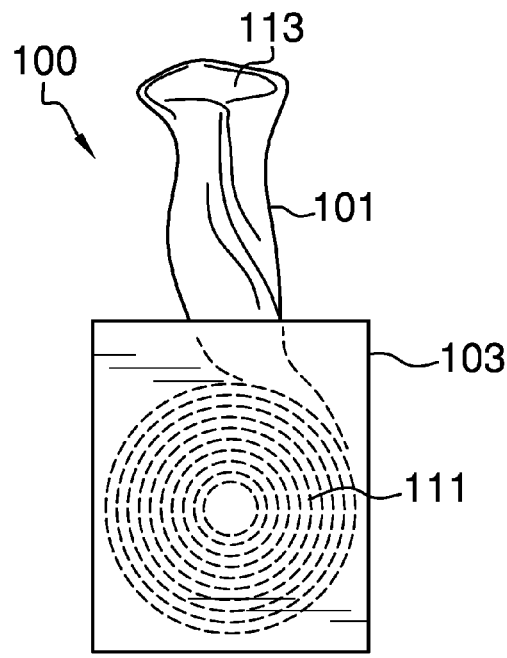
FIG. 3 is a side view of an embodiment of the disclosure.
Figure 4:
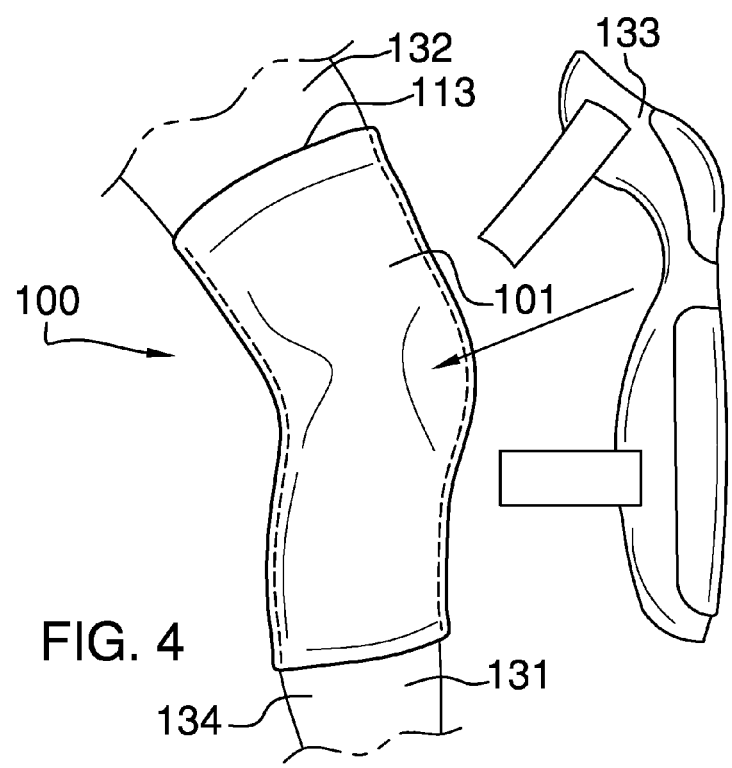
FIG. 4 is an in-use view of an embodiment of the disclosure.
Figure 5:
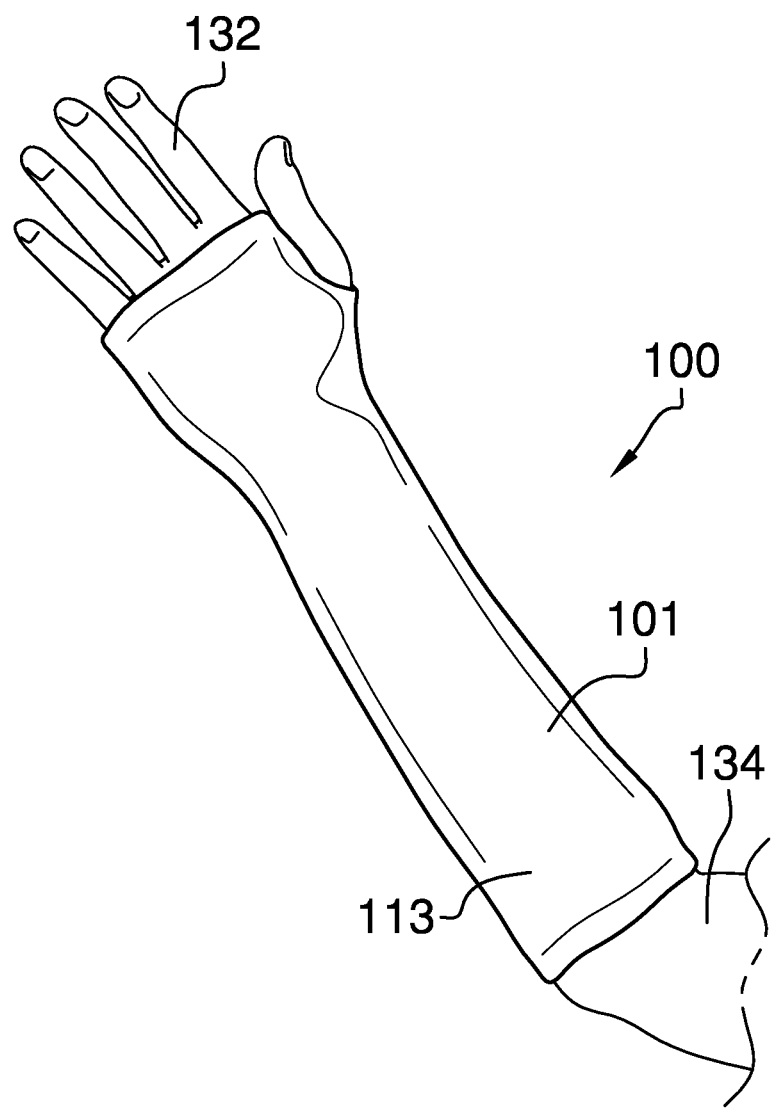
FIG. 5 is an alternative embodiment view of an embodiment of the disclosure.

Detailed reference will now be made to a several potential embodiments of the disclosure, which is illustrated in FIGS. 1 through 5. The disposable antibacterial liner 100 (hereinafter invention) is a sheath 101, intended for single use, that is designed to: 1) act as a barrier that prevents direct contact of the wearer's 131 skin 132 with personal protective equipment 133 being worn; 2) act as a prophylaxis that protects the skin 132 from infection; and, 3) treats the personal protective equipment 133 with the antimicrobial finish 102 to help keep the personal protective equipment 133 clean. The invention 100 comprises a sheath 101 and an antimicrobial finish 102.

In a first potential embodiment of the disclosure, the sheath 101 is formed from a textile. Suitable fibers for forming the textile include, but are not limited to, cotton, lyocell, nylon, or polyester. Cotton or lyocell fibers are preferred. The sheath 101 is in the form of a flexible sheet. The sheath 101 is finished with an antimicrobial finish 102 that protects the user from microbial organisms that may accumulate on the personal protective equipment 133. Suitable antimicrobial finishes include, but are not limited to, quaternary ammonium based compounds, 5-chloro-2-(2,4 dichloropheoxy) phenol, metallic salts such as copper or silver based salts, chitosan, or cyclodextrin. Methods to finish textiles with antimicrobial compounds are well known and documented in the textile arts.

In the first potential embodiment of the disclosure, the sheath 101 finished with the antimicrobial finish 102 is packaged as a roll 111 that is stored in a rectangular shaped container 103. The container 103 is formed with an access port 112. The access to the sheath 101 finished with the antimicrobial finish 102 is provided through the access port 112. Specifically, the sheath 101 finished with the antimicrobial finish 102 is drawn through the access port 112. Once the amount of sheath 101 finished with the antimicrobial finish 102 desired is drawn through the access port 112, the sheath 101 finished with the antimicrobial finish 102 is cut off the roll. To use the first potential embodiment of the disclosure, the cut sheath 101 finished with the antimicrobial finish 102 is placed on the portion of the skin 132 of the wearer 131 that will be in contact with the personal protective equipment 133. Optionally, the sheath 101 finished with the antimicrobial finish 102 can be taped into position. Once positioned, the wearer 131 puts on the personal protective equipment 133 normally. The antimicrobial finish 102 incorporated into the sheath 101 finished with the antimicrobial finish 102 will both: 1) act as a prophylaxis that protects the skin 132 from infection; and, 2) treat the personal protective equipment 133 with the antimicrobial finish 102 to help keep the personal protective equipment 133 clean.

In a second potential embodiment of the disclosure, the sheath 101, antimicrobial finish 102, and the container 103 are the same as the described in the first potential embodiment of the disclosure with the following modifications. The sheath 101 is further formed as a tubular 113 textile material. Methods to form tubular textiles are well known and documented in the textile arts. The tubular 113 sheath 101 is finished with an antimicrobial finish 102 as described in the first potential embodiment of the disclosure to form a tubular 113 sheath 101 finished with the antimicrobial finish 102. The tubular 113 sheath 101 finished with the antimicrobial finish 102 is rolled and stored in a container 103 as described in the first potential embodiment of the disclosure.

To use the second potential embodiment of the disclosure, the tubular 113 sheath 101 finished with the antimicrobial finish 102 is cut to the desired length. If the tubular 113 sheath 101 finished with the antimicrobial finish 102 is to be used on an appendage 134 of the wearer 131, the appendage 134 is inserted through the center of the tubular 113 sheath 101 finished with the antimicrobial finish 102 to protect the appendage 134. The personal protective equipment 133 is then worn normally. If the tubular 113 sheath 101 finished with the antimicrobial finish 102 is not to be used on an appendage 134, the tubular 113 sheath 101 finished with the antimicrobial finish 102 is applied as described in the first potential embodiment of the disclosure.

In a third potential embodiment of the disclosure, the tubular 113 sheath 101, antimicrobial finish 102, and the container 103 are the same as the described in the second potential embodiment of the disclosure with the following modifications: the tubular 113 sheath 101 further comprises the use of elastic yarns that are designed to allow the tubular 113 sheath 101 to apply a compressive force towards the appendage 134 that allows the tubular 113 sheath 101 to hold itself in place against the appendage 134.

In a fourth potential embodiment of the disclosure, the sheath 101, the tubular 113 sheath 101, antimicrobial finish 102, and the container 103 are the same as the described in the first potential embodiment of the disclosure, second potential embodiment of the disclosure, third potential embodiment of the disclosure, and the fourth potential embodiment of the disclosure with the following modifications. The sheath 101 and the tubular 113 sheath 101 further comprises a plurality of sets of perforations 104 wherein each individual set of perforations 114 is formed in the sheath 101 or tubular 113 sheath 101 at a predetermined fixed distance from each prior individual set of perforations 114 and from each subsequent individual set of perforations 114. Each individual set of perforations 114 comprises a series of holes that are formed in a line along the sheath 101 or tubular 113 sheath 101 in such a way as to allow the sheath 101 or the tubular 113 sheath 101 to be easily torn along the line formed by the series of holes.

The fourth potential embodiment of the disclosure is used in the same manner as the invention 100 is used in the first potential embodiment of the disclosure, second potential embodiment of the disclosure or the third potential embodiment of the disclosure. The difference is that instead of cutting the sheath 101 or the tubular 113 sheath 101, the sheath 101 or the tubular 113 sheath 101 are torn at an individual set of perforations 114 that is selected by the wearer 131.

The following definitions were used in this disclosure:

Personal Protective Equipment: As used in this disclosure, personal protective equipment refers to the use of protective garments or protective equipment that is designed to protect the wearer's body from injury. Personal protective equipment may be designed for occupational protection, including, but not limited to, equipment to protect military, police, or firefighting personnel, or may be designed to provide protection in sports or recreational activities, including, but not limited to, equipment to protect participants in football, hockey, or soccer activities.

Salt: As used in this disclosure, a salt means an ionic compound that further comprises at least one atom of a metallic element. When dissolved in water, the ionic compound releases the metallic element into the water as an ion.

Textile: As used in this disclosure, a textile is a material that is woven, knitted or felted. Synonyms in common usage for this definition of textile include fabric and cloth.

Tube: As used in this disclosure, a tube is a hollow cylindrical device with a first open end and a second open end that is used for transporting liquids and gasses.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:
1. A liner comprising:
a sheath and an antimicrobial finish;
wherein the sheath is impregnated with the antimicrobial finish;
wherein the sheath is disposable after use;
wherein the sheath is used as a liner for personal protective equipment;
wherein the sheath is adapted to act as a barrier that prevents direct contact of a wearer's skin with the personal protective equipment;
wherein the sheath with the antimicrobial finish acts as a prophylaxis in order to protect the skin from infection;

wherein the sheath with the antimicrobial finish treats the personal protective equipment with the antimicrobial finish;

wherein the sheath is further formed as a tubular textile material.

2. The liner according to claim 1 wherein the sheath is formed from a textile.

3. The liner according to claim 2 wherein the sheath is formed from fibers selected from the group consisting of cotton or lyocell.

4. The liner according to claim 2 wherein the sheath is flexible.

5. The liner according to claim 4 wherein the antimicrobial finish is selected from a group consisting of quaternary ammonium-based compounds.

6. The liner according to claim 4 wherein the sheath finished with the antimicrobial finish is packaged as a roll.

7. The liner according to claim 6 wherein the sheath finished with the antimicrobial finish is stored in a container.

8. The liner according to claim 7 wherein
the container is formed with an access port;
wherein the sheath finished with the antimicrobial finish is drawn through the access port;
wherein the sheath finished with the antimicrobial finish is cut off the roll;
wherein the sheath finished with the antimicrobial finish is placed on the portion of the skin of the wearer that will be in contact with the personal protective equipment.

9. The liner according to claim 8 wherein the tubular textile material is adapted to fit of the appendage of the wearer.

10. The liner according to claim 9 wherein the tubular textile material further comprises elastic yarns.

11. The liner according to claim 10 wherein the elastic yarns are designed to apply a compressive force towards the appendage of the wearer.

12. The liner according to claim 11 wherein the sheath further comprises a plurality of sets of perforations.

13. The liner according to claim 12 wherein each individual set of perforations is formed in the sheath at a predetermined fixed distance from each prior individual set of perforations and from each subsequent individual set of perforations.

14. The liner according to claim 13 wherein each individual set of perforations comprises a series of holes that are formed in a line along the sheath in such a way as to allow the sheath to be easily torn along the line formed by the series of holes.

15. The liner according to claim 14 wherein the sheath further comprises a plurality of sets of perforations.

16. The liner according to claim 15 wherein each individual set of perforations is formed in the sheath at a predetermined fixed distance from each prior individual set of perforations and from each subsequent individual set of perforations.

17. The liner according to claim 16 wherein each individual set of perforations comprises a series of holes that are formed in a line along the sheath in such a way as to allow the sheath to be easily torn along the line formed by the series of holes.

\* \* \* \* \*